United States Patent
Numoto et al.

[11] Patent Number: 6,141,976
[45] Date of Patent: Nov. 7, 2000

[54] MANUFACTURING METHOD OF AN AIR CONDITIONER

[75] Inventors: Hironao Numoto; Toru Yasuda; Akira Fujitaka, all of Otsu; Hiroshi Namura, Shiga, all of Japan

[73] Assignee: Matsushita Electric Industrial Co., Ltd., Osaka, Japan

[21] Appl. No.: 09/110,936

[22] Filed: Jul. 6, 1998

[30] Foreign Application Priority Data

Jul. 4, 1997 [JP] Japan ..................................... 9-179354

[51] Int. Cl.⁷ ....................................................... F25B 43/00
[52] U.S. Cl. ................................................ 62/129; 62/474
[58] Field of Search ......................... 29/840.035, 840.03, 29/428; 62/125, 126, 129, 474; 73/29.01, 29.04

[56] References Cited

U.S. PATENT DOCUMENTS

| | | | |
|---|---|---|---|
| 3,846,730 | 11/1974 | Hamilton | 62/129 X |
| 3,887,977 | 6/1975 | Riello | 29/890.035 |
| 4,110,998 | 9/1978 | Owen | 62/125 |
| 4,498,305 | 2/1985 | Bzdula | 62/129 X |
| 5,071,768 | 12/1991 | Klodowski | 62/129 X |

FOREIGN PATENT DOCUMENTS 9-203572  8/1997  Japan .

Primary Examiner—Harry B. Tanner
Attorney, Agent, or Firm—Ratner & Prestia

[57] ABSTRACT

A manufacturing method for an air conditioner including the steps of: (a) assembling a refrigeration cycle by connecting an outdoor unit, which has a compressor containing a refrigerant and an outdoor heat exchanger to a dummy indoor unit, and a part including a moisture adsorbent, using connection piping; (b) operating the refrigeration cycle by either an intermittent heating operation or switching between cooling and heating operations to adsorb moisture contained in the refrigeration cycle using a moisture adsorbent; (c) disconnecting the part including the moisture adsorbent after adsorbing moisture from the refrigeration cycle, and (d) measuring the water content contained in the moisture adsorbent, to control the water contained in the outdoor unit.

20 Claims, 3 Drawing Sheets

Assembling refrigeration cycle by connecting outdoor unit, connection piping, dummy indoor unit, and part incorporating substance having moisture adsorbing function.
(Part incorporating substance having moisture adsorbing function is disposed in at least one of connection piping and dummy indoor unit.)

By operating the refrigeration cycle, moisture contained in the refrigeration cycle is adsorbed on the substance having moisture adsorbing function.

Dismounting the part incorporating the substance having moisture adsorbing function having adsorbed moisture from the refrigeration cycle.

Water content contained in the substance having moisture adsorbing function having adsorbed moisture is measured.

FIG. 3

Assembling refrigeration cycle by connecting outdoor unit, connection piping, dummy indoor unit, first part incorporating substance having first moisture adsorbing function, and second part incorporating substance having second moisture adsorbing function.
First part incorporating the substance having first moisture adsorbing function is disposed in the outdoor unit, and second part incorporating the substance having second moisture adsorbing function is disposed in at least one of connection piping and dummy indoor unit.

By operating the refrigeration cycle, moisture contained in the refrigeration cycle is adsorbed on the substance having first moisture adsorbing function and substance having second moisture adsorbing function.

Dismounting the second part incorporating the substance having second moisture adsorbing function having adsorbed moisture from the refrigeration cycle.

Water content contained in the substance having second moisture adsorbing function having adsorbed moisture is measured.

FIG. 4

MANUFACTURING METHOD OF AN AIR CONDITIONER

FIELD OF THE INVENTION

The present invention relates to a manufacturing method of separate type air conditioner for joining an indoor unit and an outdoor unit through connection piping, and more particularly to a moisture control method for an air conditioner.

BACKGROUND OF THE INVENTION

In a conventional manufacturing method of an air conditioner, moisture was controlled in the following method. A refrigerant (R22, HCFC: hydrochlorofluorocarbon) is poured into the main body of the outdoor unit. The outdoor unit is then checked for refrigerant leaks. In the final process, to inspect the product characteristics, a dummy indoor unit is connected to the outdoor unit, and the system is inspected. When no problems are found, the product is completed. As a moisture control method in the man turning process, a specific amount of refrigerant is sampled, and the water content in the refrigerant sample is measured. That is, as mineral oil having a low moisture adsorption has been used as a compressor oil, it was sufficient to control only the moisture rate contained in the refrigerant in the refrigeration cycle.

Recently, however, as the environmental regulations have become stricter due to the destruction of the ozone layer and global warming, there is an urgent need for development of air conditioner using chlorine-free HFC (hydrofluorocarbon). Since the HFC refrigerant does not contain chlorine, it does not exhibit the lubricating quality of the conventional HCFC. Hence, the oil to be contained in an enclosed container is particularly required to be an oil compatible with an HFC refrigerant. The oil contained in an enclosed container is stirred by the HFC refrigerant discharged from the compression mechanism into the enclosed container, and is further stirred by a rotor of a motor. At this time, since the oil and refrigerant are compatible, the oil sufficiently accompanies the refrigerant discharged into the enclosed container, and sufficiently permeates the small parts of the sliding members of the machine. Therefore, together with the supply of oil from the oil pump, the lubricating performance is enhanced. As such oil, synthetic oil such as ester oil or ether oil as disclosed, for example, in Japanese Laid-open Patent No. 6-235570 has come to be used.

However, both ester oil and ether oil have a high moisture adsorption, and when used in a compressor containing such an oil, it is necessary to manufacture the air conditioner (outdoor unit) under stricter moisture control than before.

In the light of the problems of the moisture control in manufacturing the air conditioner using an HFC refrigerant in the conventional manufacturing method, it is an object of the invention to present a manufacturing method capable of controlling moisture of product sufficiently in a simple method.

SUMMARY OF THE INVENTION

A manufacturing method of an air conditioner according to the invention comprises:
 an outdoor unit including a compressor containing a refrigerant and an outdoor heat exchanger,
 an indoor unit including an indoor heat exchanger, and a connection piping for joining the outdoor unit and the indoor unit, and circulating the refrigerant therein,
in which the manufacturing method comprises the steps of: (a) assembling a refrigeration cycle by connecting the outdoor unit, the connection piping, a dummy indoor unit, and a part including a substance having moisture adsorbing function,
 (b) operating the refrigeration cycle for adsorbing the moisture contained in the refrigeration cycle on the substance having moisture adsorbing function,
 (c) dismounting the part incorporating a substance having adsorbed moisture from the refrigeration cycle, and
 (d) measuring the water content contained in the substance having adsorbed moisture,
  wherein these water content contained in the outdoor unit is controlled.

Preferably, the part incorporating the substance having a moisture adsorbing function is composed in at least one of (i) the dummy indoor unit and (ii) the path of the connection piping.

Preferably, the part incorporating the substance having the moisture adsorbing function comprises a first part incorporating a substance having first moisture adsorbing function, and a second part incorporating a substance having second moisture adsorbing function, the first part is installed in the outdoor unit, and the second part incorporating the substance having the second moisture adsorbing function is disposed in at least one of (i) the dummy indoor unit and (ii) the path of the connection piping.

Preferably, the refrigerant contains hydrofluorocarbon.

Preferably, the compressor contains at least one of ester oil and ether oil as a lubricating oil.

In this way, the absolute amount of water content contained in an outdoor unit can be easily controlled.

BRIEF DESCRIPTION OF THE DRAWINGS

FIG. 3 is a process diagram for a manufacturing method of an air conditioner in an embodiment of the present invention.

FIG. 4 is a process diagram in a manufacturing method of an air conditioner in another embodiment of the present invention.

DETAILED DESCRIPTION OF THE INVENTION

Figure 1:
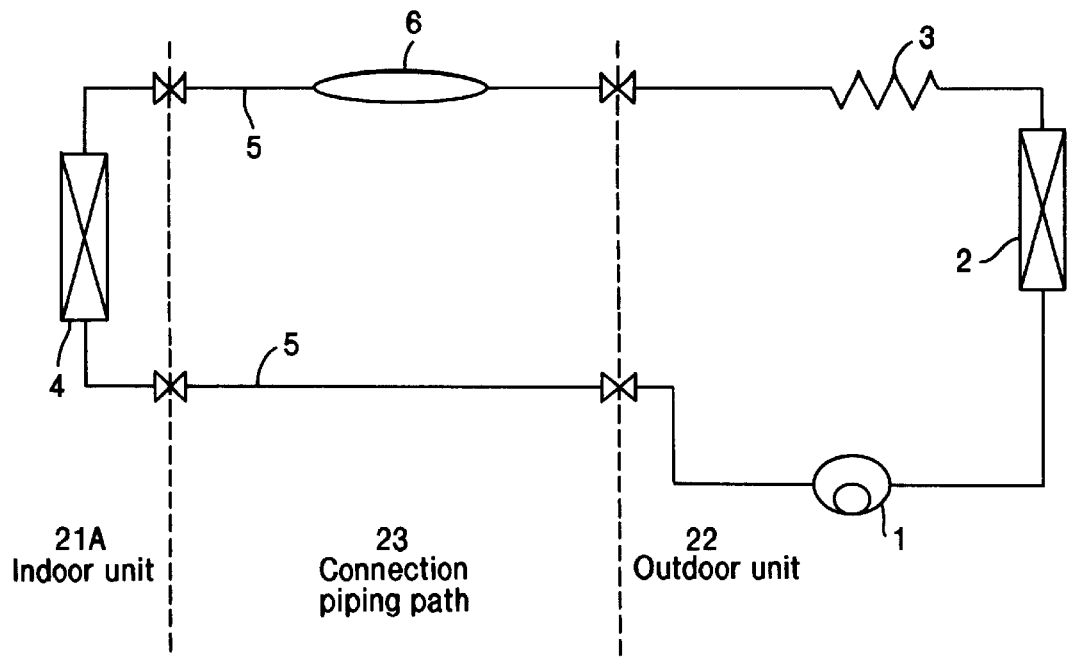
FIG. 1 is a moisture control process block diagram in a manufacturing method of an air conditioner according to a first exemplary embodiment of the present invention.

The manufacturing method for an air conditioner according to the invention is characterized by assembling a refrigeration cycle by connecting an outdoor unit to a dummy indoor unit. A part incorporating a substance having moisture adsorbing function is disposed in a connection piping path or in the dummy indoor unit followed by operating the system through a refrigeration cycle to adsorb the moisture contained in the refrigerant stored in the main body of the outdoor unit. The part incorporating the substance having moisture adsorbing function is then removed from the connection piping path or dummy indoor unit, and the water adsorbed by the substance having the moisture adsorbing function is measured. In this way, the water content in the air conditioner outdoor unit is controlled. Furthermore, using this method the absolute moisture in the completed outdoor unit can be measured relatively easily. After measuring the moisture, the outdoor unit can be presented to the market as product.

Another manufacturing method of the air conditioner according to the invention is characterized by assembling a refrigeration cycle by connecting an indoor unit and an outdoor unit with a connection piping. A first part incorporating a substance having a first moisture adsorbing function is disposed in the main body of the outdoor unit. The outdoor unit is connected to a dummy indoor unit, and a second part incorporating a substance having a second moisture adsorbing function is disposed in the connection piping path or in the dummy indoor unit. The refrigeration cycle is then operated to adsorb the moisture contained in the refrigerant of the outdoor unit main body by the substances having the first and second moisture adsorbing function. The second part incorporating the substance having the second moisture adsorbing function is then removed from the connection piping path or dummy indoor unit, and the water content adsorbed by the substance having the second moisture adsorbing function is measured. In this way, the water content of the air conditioner outdoor unit is controlled. In this method, the water content contained in the outdoor unit main body is almost evenly adsorbed by the first part incorporating the substance having the first moisture adsorbing function and the second part incorporating the substance having the second moisture adsorbing function. Therefore, by measuring the water content in the second part incorporating the substance having the second moisture adsorbing function, the moisture contained in the outdoor unit main body can be estimated.

In a different manufacturing method of an air conditioner according to the invention, a continuous heating operation is performed in order to adsorb moisture contained in the refrigeration cycle in the outdoor unit main body by a part incorporating a substance having a moisture adsorbing function. In this method, the refrigerant repeats a circulation and stagnation cycle more than in a continuous operation, and the moisture is more readily adsorbed by the substance having the moisture adsorbing function.

In a different manufacturing method of air conditioner of the invention, a cooling-heating changeover operation is performed in order to adsorb the moisture contained in the refrigeration cycle in the outdoor unit main body by a part incorporating the substance having the moisture adsorbing function. In this method, moisture mixing in every corner in the refrigeration cycle is promptly diffused, and is adsorbed by the substance having the moisture adsorbing function.

In a further different manufacturing method of an air conditioner of the invention, the substance having a second moisture adsorbing function has a larger weight than the substance having the first moisture adsorbing function. In this method, more moisture is adsorbed by the part incorporating the substance having the second moisture adsorbing function, and the precision of estimating the moisture in the outdoor unit main body is enhanced.

In still another different manufacturing method of the air conditioner of the invention, the refrigerant passage area through the substance having the second moisture adsorbing function is smaller than the refrigerant passage area through the substance having the first moisture adsorbing function. In this way, more moisture is adsorbed by the part incorporating the substance having the second moisture adsorbing function, and the precision of estimating the moisture in the outdoor unit main body is further enhanced.

Referring now to the drawings, preferred embodiments of the invention are described below.

Exemplary Embodiment 1

FIG. 1 shows an air conditioner in an exemplary embodiment of the present invention. FIG. 3 shows a process diagram of a manufacturing method of an air conditioner in an embodiment of the invention. In FIG. 1 and FIG. 3, an outdoor unit 22 is assembled by including a compressor 1 containing a refrigerant (not shown), an outdoor heat exchanger 2 and a throttling device 3. A dummy indoor unit 21A having an indoor heat exchanger 4 is assembled. The outdoor unit 22 and dummy indoor unit 21A are connected using a connection piping path 23 having a part 6 including a substance having a moisture adsorbing function and a connection piping 5, and a refrigeration cycle is assembled. HFC is used as the refrigerant and ester oil is used in the compressor 1. Assuming a work in process, compressor 1 is allowed to stand at a temperature of 35° C. and 85% humidity for 40 hours after opening the compressor 1.

In the manufacturing process, the moisture control was inspected as follows. By operating the refrigeration cycle, the moisture contained in the refrigeration cycle was adsorbed by the substance having the moisture adsorbing function. As the operation of the refrigeration cycle, a heating operation was continuously performed for 4 hours. For part 6 including the substance having moisture adsorbing function, a part incorporating zeolite in nearly a completely dry state was disposed in the connection piping path 23. The system was then pumped down, and the outdoor unit 22 was isolated. Later, the part 6 containing the substance having the adsorbing function was disconnected from the refrigeration cycle. Then, by heating the part 6 incorporating zeolite, the water content adsorbed by the zeolite was measured using the Karl Fischer method. As a result, the water content adsorbed by the zeolite was 240 mg. After pumping down the system, the moisture content of the refrigerant in the outdoor unit 22 was measured, and the internal moisture was measured by detaching the compressor 1. Other moisture remaining in the refrigeration cycle was measured while purging with dry nitrogen. As a result, the residual moisture in the main body of the outdoor unit 22 was 60 mg. That is, it was found that about 80% of moisture in the completed outdoor unit 22 of the embodiment is adsorbed by the zeolite. Therefore, by measuring the water content adsorbed by the substance having adsorbing function, it was known that the moisture in the completed product of outdoor unit can be controlled. By closing the open pipe of the refrigeration cycle of the isolated outdoor unit 22, the closed outdoor unit 22 is shipped as a completed product.

Comparative Example 1

An air conditioner was manufactured using the same compressor and the same constitution as in embodiment 1, except that the part containing the substance having the moisture adsorbing function was not installed. The refrigeration cycle was driven by a heating operation in the same condition as in embodiment 1. A specific amount of refrigerant was extracted from the refrigeration cycle, and the water content contained in the extracted refrigerant was measured. Thus, only the moisture rate in the refrigerant was measured. As a result, the water content in the outdoor unit main body was about 50 mg as judged from the analysis of the moisture rate in the refrigerant.

In comparison between embodiment 1 and the comparative example 1, it is known that the accurate water content in the outdoor unit main body can be easily measured using the method of embodiment 1.

Exemplary Embodiment 2

An air conditioner was manufactured using the same compressor and the same conditions as in embodiment 1. A heating operation was continuously performed for 27 minutes. Then the operation was temporarily stopped, and then the heating operation was continued for an additional 3 hours and 30 minutes. The system was then pumped down. By heating the part incorporating the zeolite, the water content adsorbed by the zeolite was measured. As a result, the water content adsorbed by the zeolite was 250 mg. The residual moisture in the main body of the outdoor unit 22 was 60 mg.

Comparative Example 2

An air conditioner was manufactured using the same compressor and the same constitution as in embodiment 2, except that the part containing the substance having the moisture adsorbing function was not installed. The refrigeration cycle was driven by an intermittent heating operation in the same condition as in embodiment 2. A specific amount of refrigerant was extracted from the refrigeration cycle, and the water content contained in the extracted refrigerant was measured. Thus, only the moisture rate in the refrigerant was measured. As a result, the water content in the outdoor unit main body was about 50 mg as judged from the analysis of the moisture rate in the refrigerant.

In comparison between embodiment 2 and comparative example 2, it is known that the accurate water content in the outdoor unit main body can be easily measured using the method of embodiment 2.

Exemplary Embodiment 3

An air conditioner was manufactured using the same compressor and under the same conditions as in embodiment 1. It was operated for 3 hours repeating the cycle consisting of 22 minutes of heating and 5 minutes of cooling. The system was then pumped down. By heating the part incorporating the zeolite, the water content adsorbed by the zeolite was measured. As a result, the water content adsorbed by the zeolite was 270 mg. The residual moisture in the main body of the outdoor unit 22 was 60 mg.

Comparative Example 3

An air conditioner was manufactured using the same compressor and the same constitution as in embodiment 3, except that the part containing the substance having the moisture adsorbing function was not installed. The refrigeration cycle was driven by cooling-heating changeover operation using the same conditions as in embodiment 3. A specific amount of refrigerant was extracted from the refrigeration cycle, and the water content contained in the extracted refrigerant was measured. Thus, only the moisture rate of the refrigerant was measured. As a result, the water content in the outdoor unit main body was about 50 mg as judged from the analysis of the moisture rate in the refrigerant.

In comparison between embodiment 3 and comparative example 3, it is known that the accurate water content in the outdoor unit main body can be easily measured using the method of embodiment 3.

An intermittent heating intermittent operation was performed in embodiment2, and a cooling-heating changeover operation was performed in embodiment 3. In these operating conditions, the refrigerant does not always circulate constantly. When the refrigerant circulates at a constant speed, moisture is likely to be forced out from stagnant points, being hard to diffuse in the liquid cycle, so that diffusion is improved. As a result, more moisture can be captured in a shorter time. By enhancing the capturing rate, the precision of moisture control in the completed product is also enhanced. By using a cooling-heating changeover operation, the refrigerant circulates more easily in the bypass circuit of the liquid cycle or a circuit incorporating a check valve. As a result, moisture adsorption by the zeolite is promoted.

Exemplary Embodiment 4

Figure 2:
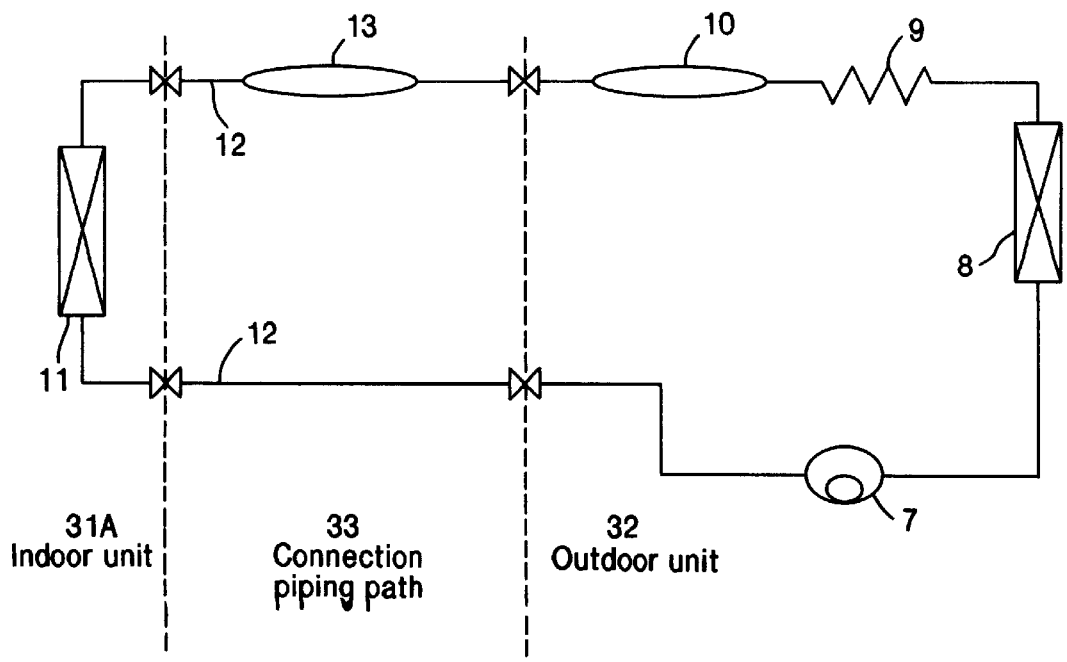
FIG. 2 is a moisture control process block diagram in a manufacturing method of an air conditioner according to a second exemplary embodiment of the present invention.

FIG. 2 shows an air conditioner in other embodiment of the invention. FIG. 4 shows a process diagram of a manufacturing method of the air conditioner in other embodiment of the invention. In FIG. 2 and FIG. 4, an outdoor unit 32 is assembled by including a compressor 7 containing a refrigerant (not shown), an outdoor heat exchanger 8, a throttling device 9, and a first part 10 including a substance having a first moisture adsorbing function. A dummy indoor unit 31A having an indoor heat exchanger 11 is assembled. The outdoor unit 32 and dummy indoor unit 31A are connected by using a connection piping path 33 having a part 13 including a substance having a second moisture adsorbing function and a connection piping 12, and a refrigeration cycle is assembled. Assuming a work in process, the compressor is allowed to stand under the conditions of a temperature of 35° C. and 85% humidity for 40 hours after opening the comparator. As the part 10 incorporating the substance having the first moisture adsorbing function and the part 13 incorporating the substance having the second moisture adsorbing function, in order to clarify the effect of the invention, each part incorporated 20 g of zeolite in nearly a completely dry state.

In this embodiment, the first part 10 incorporating the substance having the first moisture adsorbing function is installed in the outdoor unit 32 and the second part 13 incorporating the substance having the second moisture adsorbing function is installed in the connection piping path 33. The air conditioner was manufactured using the same compressor and under the same conditions as in embodiment 1 in all other respects. It was operated for 3 hours by repeating a cycle consisting of 22 minutes of heating and 5 minutes of cooling. The system was then pumped down. The second part 13 containing the second substance having adsorbed moisture was removed from the refrigeration cycle. By heating the zeolite in the part 13 having the second moisture adsorbing function, the water content adsorbed by the zeolite was measured. As a result, the water content adsorbed by the part having the second moisture adsorbing function was 135 mg. After pumping down the system, the outdoor unit was isolated, and the moisture in the refrigerant in the outdoor unit was measured. Further, dismounting the compressor 7 and the part 10 incorporating the substance having the first moisture adsorbing function, the internal moisture in the compressor 7 was measured. Other moisture remaining in the refrigeration cycle was measured while purging out with dry nitrogen. As a result, the residual moisture in the main body of the outdoor unit was 30 mg. By heating the zeolite in the part 10 having the first moisture adsorbing function, the water content adsorbed by the zeolite was measured. As a result, the water content adsorbed on the part having the first moisture adsorbing function was 135 mg.

The part 10 having the first moisture adsorbing function in the outdoor unit is known to adsorb nearly the same amount of moisture as the part 13 having the second moisture adsorbing function installed in the connection piping path 33. Also it is found that about 90% of moisture in the completed product of the outdoor unit is adsorbed by the zeolite in the part 10 having the first moisture adsorbing function and the part 13 having the second moisture adsorbing function. On the basis of this result, therefore, it was known that the moisture in the completed product can be controlled. The isolated outdoor unit is then shipped as a completed product. Besides, by dismounting the first part having the first moisture adsorbing function from the isolated outdoor unit, the outdoor unit without the first part having the first moisture adsorbing function can be shipped as a completed product.

Exemplary Embodiment 5

In the same refrigeration cycle constitution as in FIG. 2, 20 g of zeolite was used in the part 10 having the first moisture adsorbing function, and 40 g of zeolite was used in the part 13 having the second moisture adsorbing function. Assuming a work in process, the compressor 7 is allowed to stand under the conditions of 35° C. and 85% humidity for 40 hours after opening compressor 7. As the part 10 incorporating the substance having the first moisture adsorbing function and the part 13 incorporating the substance having the second moisture adsorbing function, in order to clarify the effect of the invention, each part incorporated zeolite in nearly a completely dry state. As in embodiment 4, the system was operated for 3 hours by repeating a cycle consisting of 22 minutes of heating and 5 minutes of cooling, and it was then pumped down. By heating the zeolite in the part 13 having the second moisture adsorbing function, the water content adsorbed by the zeolite was measured. As a result, the water content adsorbed by the part having the second moisture adsorbing function was 180 mg. After pumping down, the moisture in the refrigerant in the outdoor unit was measured. Further, dismounting the compressor 7 and the part 10 incorporating the substance having the first moisture adsorbing function, the internal moisture in the compressor 7 was measured. Other moisture remaining in the refrigeration cycle was measured while purging with dry nitrogen. As a result, the residual moisture in the main body of the outdoor unit was 30 mg. By heating the zeolite in the part 10 having the first moisture adsorbing function, the water content adsorbed by the zeolite was measured. As a result, the water content adsorbed by the part having the first moisture adsorbing function was 90 mg.

Therefore, in the part 10 having the first moisture adsorbing function in the outdoor unit and the part 13 having the second moisture adsorbing function installed in the connection piping path, it is known that moisture in the refrigeration cycle is adsorbed in proportion to the ratio of weight of the incorporated zeolite. Also, in this embodiment, about 90% of the moisture in the completed outdoor unit is adsorbed by the zeolite in the part 10 having the first moisture adsorbing function and the part 13 having the second moisture adsorbing function. As a result, about 60% of the moisture in the completed product is known by measuring the water content adsorbed by the zeolite in the part 13 having the second moisture adsorbing function, and it is found that the entire moisture can be controlled on the basis thereof.

Exemplary Embodiment 6

In the same refrigeration cycle constitution as in FIG. 2, 20 g of zeolite was used in the part 10 having the first moisture adsorbing function. The refrigerant passage area for passage through the incorporated zeolite was about 5 $CM^2$. In the part 13 having the second moisture adsorbing function, 40 g of zeolite was used. The refrigerant passage area for passage through the incorporated zeolite was about 2 $CM^2$. Using an air conditioner, such as in embodiment 4, it was operated for 3 hours by repeating a cycle consisting of 22 minutes of heating and 5 minutes of cooling. The system was then pumped down. At this time, assuming a work in process, compressor 7 was allowed to stand under the conditions of 35° C. and 85% humidity for 40 hours after opening the compressor 7. As the part 10 incorporating the substance having the first moisture adsorbing function and the part 13 incorporating the substance having the second moisture adsorbing function, in order to clarify the effect of the invention, the parts incorporated zeolite in nearly a completely dry state. By heating the zeolite in the part 13 having the second moisture adsorbing function, the water content adsorbed by the zeolite was measured. As a result, the water content was 210 mg. After pumping down the system, the moisture in the refrigerant in the outdoor unit was measured. Further, dismounting the compressor and the part 10 incorporating the substance having the first moisture adsorbing function, the internal moisture was measured. Other moisture remaining in the refrigeration cycle was measured while purging with dry nitrogen. As a result, the residual moisture in the main body of the outdoor unit was 30 mg. By heating the zeolite in the part 10 having the first moisture adsorbing function, the water content adsorbed by the zeolite was measured. As a result, the water content adsorbed by the part having the first moisture adsorbing function was 60 mg.

Therefore, when the moisture adsorbed by the zeolite incorporated in the part 10 having the first moisture adsorbing function in the outdoor unit and the zeolite incorporated in the part 13 having the second moisture adsorbing function installed in the connection piping path are compared, it is known that more moisture in the refrigeration cycle is adsorbed by the part having the smaller passage area for passing the refrigerant. It is also found that about 90% of the moisture in the completed product of outdoor unit is adsorbed by the zeolite in the part 10 having the first moisture adsorbing function and the part 13 having the second moisture adsorbing function. As a result, about 70% of the moisture in the completed product is known by measuring the water content adsorbed by the zeolite in the part 13 having the second moisture adsorbing function, and it is found that the entire moisture can be controlled on the basis thereof.

Exemplary Embodiment 7

FIG. 3 shows a process diagram of a manufacturing method of air conditioner in an embodiment of the invention. In FIG. 3, an outdoor unit is assembled by including a compressor 1 (shown in FIG. 1) containing refrigerant, an outdoor heat exchanger, and a throttling device. A dummy indoor unit 21A (shown in FIG. 1) having an indoor heat exchanger and a part including a substance having a moisture adsorbing function is assembled. The outdoor unit 22 and dummy indoor unit 21A are connected by using a connection piping path 23 having a connection piping 5, and a refrigeration cycle is assembled. At this time, a compressor using ester oil was used. Assuming a work in process, compressor 1 is allowed to stand at a temperature of 35° C. and 85% humidity for 40 hours after opening comparator 1.

In the manufacturing process, the moisture control was inspected as follows. By operating the refrigeration cycle, the moisture contained in the refrigeration cycle was adsorbed by the substance having moisture adsorbing function. The refrigeration cycle consisted of a heating operation continuously performed for 4 hours. As the part containing the substance having the moisture adsorbing function, a part incorporating zeolite in a nearly completely dry state was used. The system was then pumped down. Later, the part containing the substance having the adsorbed moisture was dismounted from the refrigeration cycle. Then, by heating the part incorporating the zeolite, the water content adsorbed by the zeolite was measured using the Karl Fischer method. As a result, the water content was 240 mg.

After pumping down the system, the moisture in the refrigerant in the outdoor unit was measured, and the internal moisture was measured by detaching the compressor. Other moisture remaining in the refrigeration cycle was measured while purging with dry nitrogen. As a result, the residual moisture in the main body of the outdoor unit was 60 mg. That is, it is found that about 80% of moisture in the completed outdoor unit according to the embodiment is adsorbed by the zeolite. Therefore, on the basis of this result, it was known that the moisture in the completed product can be controlled.

In embodiments 1 to 7, effects of the invention are disclosed for an air conditioner using ester oil. The invention is not limited to this, however, and the air conditioner may use other oils such as ether oil. Furthermore, similar results were obtained by disposing a part incorporating other substances having moisture adsorbing properties.

In embodiments 1 to 6, the part incorporating the substance having the moisture adsorbing mechanism is disposed in the connection piping path. The invention is not limited to this, however, and as shown in embodiment 7, similar effects may be obtained by disposing a part incorporating a substance having a moisture adsorbing function in the dummy indoor unit. In this case, however, it was slightly more complicated when compared with the case of detaching and attaching the part incorporating the substance having the moisture adsorbing function.

In the foregoing embodiments, zeolite was used as the substance having moisture adsorbing function. The invention is not limited to this, however, as other substances having a moisture adsorbing function may be used, such as silica gel, calcium chloride, and water adsorbing polymer.

In the embodiments, as the method of adsorbing moisture contained in the refrigeration cycle by the substance having the moisture adsorbing function, examples of intermittent heating operations and cooling-heating changeover operations are shown. The invention is not limited to these, however, as a continuous heating operation and intermittent cooling operations are also possible, and that by using these methods the water content in the outdoor unit can be easily controlled.

As is clear from these embodiments, in the constitution of the invention, the absolute moisture in the completed outdoor unit can be measured easily and accurately. Even after measuring the moisture, the outdoor unit used in measurement can be presented to the market as a product.

The water content contained in the outdoor unit main body is adsorbed almost evenly in the part incorporating the substance having the first moisture adsorbing function and in the part incorporating the substance having the second moisture adsorbing function, and therefore by measuring the water content in the part incorporating the substance having the second moisture adsorbing function, the moisture in the outdoor unit main body can be estimated.

By using an intermittent heating operation for adsorbing moisture contained in the refrigeration cycle in the outdoor unit main body by the part incorporating the substance having moisture adsorbing function, when compared to a continuous operation, the refrigerant repeats circulation and stagnation more in the refrigeration cycle, and the moisture is adsorbed by the substance having the moisture adsorbing function more promptly and effectively.

By using a cooling-heating changeover operation for adsorbing moisture contained in the refrigeration cycle in the outdoor unit main body by the part incorporating the substance having the moisture adsorbing function, moisture mixed in every corner of refrigeration cycle is diffused promptly, and is adsorbed by the substance having the moisture adsorbing function. For example, this may be was particularly effective in systems having a bypass circuit or a check valve circuit.

By allowing the weight of substance having the second moisture adsorbing function to be greater than that of the substance having first moisture adsorbing function, more moisture is adsorbed by the part incorporating the substance having the second moisture adsorbing function. This tendency is determined by the ratio of weight, and by increasing the ratio, the precision of estimating the moisture in the outdoor unit main body is enhanced.

By setting the passage area of the refrigerant passing through the substance having second moisture adsorbing function smaller than the passage area of the refrigerant passing through substance having first moisture adsorbing function, more moisture is adsorbed on the part incorporating the substance having second moisture adsorbing function. By increasing the ratio of passage area, the precision of measuring the moisture in the outdoor unit main body is enhanced.

Although preferred embodiments of the invention have been shown and described, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

What is claimed is:

1. A method of measuring moisture content of an air conditioner, said method comprising the steps of:
 (a) disposing a part having a moisture adsorbent in said air conditioner,
 (b) operating said air conditioner so that moisture produced by said air conditioner is adsorbed by the moisture adsorbent,
 (c) measuring said moisture contained in the moisture adsorbent to obtain said moisture content.

2. The method according to claim 1, wherein said part comprises a first part having a first moisture adsorbent and a second part having a second moisture adsorbent.

3. The method according to claim 1, wherein said step (b) includes at least one of i) a heating operation, ii) an intermittent heating operation, iii) a cooling-heating changeover operation, iv) a cooling operation, and v) an intermittent cooling operation.

4. The method according to claim 1, further comprising a step of i) separating the outdoor unit from the refrigeration cycle, after operating the refrigeration cycle and adsorbing the moisture contained in the refrigeration cycle by the moisture adsorbent.

5. The method according to claim 1, wherein the moisture adsorbent is selected from the group consisting of zeolite, silica gel, and calcium chloride.

6. The method according to claim 1, further comprising the step of removing said part from said air conditioner prior to measuring said moisture in the moisture absorbent.

7. A method of measuring moisture content of an air conditioner, said air conditioner having (1) an outdoor unit, (2) an indoor unit, and (3) a connection piping joining said outdoor unit and said indoor unit, said method comprising the steps of:

(a) connecting said outdoor unit, said connection piping, a dummy indoor unit, and a part having a moisture adsorbent to provide a refrigeration cycle, said part being disposed in at least one of (i) said dummy indoor unit and (ii) said connection piping, (b) operating said refrigeration cycle, wherein said refrigeration cycle produces moisture and wherein said moisture is adsorbed by the moisture adsorbent, and (c) measuring said moisture contained in the moisture adsorbent to obtain said moisture content.

8. The method according to claim 7, wherein said step (b) is an intermittent heating operation.

9. The method according to claim 7, wherein said step (b) is a cooling-heating changeover operation.

10. The method according to claim 7, further comprising the step of removing said part from said refrigeration cycle prior to measuring said moisture in the moisture absorbent.

11. The method according to claim 7, wherein a refrigerant circulates within said connection piping.

12. A method of measuring moisture content of an air conditioner, said air conditioner having (1) an outdoor unit, (2) an indoor unit, and (3) a connection piping joining said outdoor unit and said indoor unit, said method comprising the steps of:

(a) providing a refrigeration cycle by connecting said outdoor unit, said connection piping, a dummy indoor unit, a first part installed in said outdoor unit, said first part having a first moisture adsorbent, and a second part disposed in at least one of (i) said dummy indoor unit and (ii) a route of said connection piping, said second part having a second moisture adsorbent, (b) operating said refrigeration cycle, wherein said refrigeration cycle produces moisture and wherein said moisture is adsorbed by the first moisture adsorbent and the second moisture adsorbent, and (c) measuring said moisture contained in the second moisture adsorbent to obtain said moisture content.

13. The method according to claim 12, wherein operating said refrigeration cycle is an intermittent heating operation.

14. The method according to claim 12, wherein operating said refrigeration cycle is a cooling-heating changeover operation.

15. The method according to claim 12, wherein in step (a), the second moisture adsorbent has a greater weight than the first moisture adsorbent.

16. The method according to claim 12, wherein a refrigerant passage area of said first part is greater than a refrigerant passage area of said second part.

17. The method according to claim 12, further comprising the step of removing said part from said refrigeration cycle prior to measuring said moisture content.

18. The method according to claim 12, wherein a refrigerant circulates within said connection piping.

19. The method according to claim 18, wherein said refrigerant contains a hydrofluorocarbon.

20. The method according to claim 18, wherein said refrigerant contains a hydrofluorocarbon, and said compressor contains at least one of an ester oil and an ether oil.

* * * * *